US007244432B2

(12) United States Patent
Vakharia

(10) Patent No.: US 7,244,432 B2
(45) Date of Patent: Jul. 17, 2007

(54) INFECTIOUS BURSAL DISEASE VIRUS (IBDV) VARIANT FROM GEORGIA

(75) Inventor: Vikram Vakharia, Bowie, MD (US)

(73) Assignee: University of Maryland Biotechnology Institute, Baltimore, MD (US)

( * ) Notice: Subject to any disclaimer, the term of this patent is extended or adjusted under 35 U.S.C. 154(b) by 0 days.

(21) Appl. No.: 11/170,056

(22) Filed: Jun. 29, 2005

(65) Prior Publication Data

US 2006/0121567 A1 Jun. 8, 2006

Related U.S. Application Data

(60) Provisional application No. 60/634,186, filed on Dec. 8, 2004.

(51) Int. Cl.
*A61K 31/12* (2006.01)
*C12N 7/00* (2006.01)

(52) U.S. Cl. .................. 424/186.1; 435/235.1; 424/204.1

(58) Field of Classification Search .................. 514/44; 424/139.1, 199.1
See application file for complete search history.

(56) References Cited

U.S. PATENT DOCUMENTS

| 5,064,646 A | 11/1991 | Snyder |
| 5,472,858 A | 12/1995 | Attie et al. |
| 5,518,724 A | 5/1996 | Snyder, et al. |
| 5,595,912 A | 1/1997 | Vakharia et al. |
| 5,632,989 A | 5/1997 | Snyder et al. |
| 5,788,970 A | 8/1998 | Vakharia et al. |
| 5,871,744 A | 2/1999 | Vakharia et al. |
| 6,017,759 A | 1/2000 | Vakharia et al. |
| 6,087,165 A | 7/2000 | Raina et al. |
| 6,156,314 A | 12/2000 | Vakharia et al. |
| 6,231,868 B1 | 5/2001 | Vakharia et al. |
| 6,274,147 B1 | 8/2001 | Vakharia et al. |
| 6,596,280 B1 | 7/2003 | Vakharia et al. |
| 6,936,256 B2 | 8/2005 | Vakharia |
| 2003/0072772 A1 | 4/2003 | Vakharia |

FOREIGN PATENT DOCUMENTS

WO     WO 9116925 A1 * 11/1991

OTHER PUBLICATIONS

Caston et al., "C Terminus of Infectious Bursal Diseas Virus Major Capsid Protein VP2 Is Involved in Definition of the T Number for Capsid Assembly," Journal of Virology, Nov. 2001, vol. 75, No. 22, pp. 10815-10828.*

Kato et al., "Identification and characterization of Marek's disease virus serotype 1 (MDV1) ICP22 gene product: MDV1 ICP22 transactivates the MDV1 ICP27 promoter syneergistically with MDV1 ICP4," Veterinary Microbiology vol. 85, p. 305-313 (2002).*

(Continued)

*Primary Examiner*—Bruce R. Campell
*Assistant Examiner*—M. Franco Salvoza
(74) *Attorney, Agent, or Firm*—Steven J. Hultquist; Intellectual Property /Technology Law; Kelly K. Reynolds

(57) ABSTRACT

A VP2 protein isolated from a variant Georgia strain of Infectious Bursal Disease Virus (IBDV) and method of generating such VP2 protein and variant strain for use to reduce or prevent infection in poultry by IBDV.

13 Claims, 3 Drawing Sheets

```
   1  ATGACAAACC TGCAAGATCA AACCCAACAG ATTGTTCCGT TCATACGGAG CCTTCTGATG
  61  CCAACAACCG GACCGGCGTC CATTCCGGAC GACACCCTGG AGAAGCACAC TCTCAGGTCA
 121  GAGACCTCGA CCTACAATTT GACTGTGGGG GACACAGGGT CAGGGCTAAT TGTCTTTTTC
 181  CCTGGATTCC CTGGCTCAAT TGTGGGTGCT CACTACACAC TGCAGAGCAA TGGGAACTAC
 241  AAGTTCGATC AGATGCTCCT GACTGCCCAG AACCTACCTG CCAGCTACAA CTACTGCAGG
 301  CTAGTGAGTC GGAGTCTCAC AGTAAGGTCA AGCACACTCC CTGGTGGCGT TTATGCACTA
 361  AACGGCACCA TAAACGCCGT GACCTTCCAA GGAAGCCTGA GTGAACTGAC AGATGTTAGC
 421  TACAATGGAT TGATGTCTGC GACAGCCAAC ATTAACGACA AAATTGGGAA CGTCCTAGTA
 481  GGGGAAGGGG TAACCGTCCT CAGCTTACCC ACATCATATG ATCTTGGGTA TGTGAGGCTT
 541  GGCGACCCCA TACCTGCTAT AGGGCTTGAC CCAAAAATGG TAGCAACATG TGACAGCAGT
 601  GACAGGCCCA GAGTCTACAC CATAACCGCA GCCGATAATT ACCAATTCTC ATCACAGTAC
 661  CAAACAGGCG GGGTAACAAT CACACTGTTC TCAGCCAACA TTGATGCCAT CACAAGTCTC
 721  AGTGTTGGGG GAGAGCTCGT GTTCAAAACA AGCGTCCAAA GCCTTGTACT GGGCGCCACC
 781  ATCTACCTTA TAGGCTTTGA TGGGACTGCG GTGATCACCA GAGCTGTGGC CGCAAACAAT
 841  GGGCTGACGG CCGGCATCGA CAATCTTATG CCATTCAATC TTGTGATTCC AACCAATGAA
 901  ATAACCCAGC CAATCACATC CATCAAACTG GAGATAGTGA CCTCCAAAAG TAATGGTCAG
 961  GAGGGGGACC AGATGTCATG GTCGGCGAGT GGGAGCCTAG CAGTGACGAT CCATGGTGGC
1021  AACTATCCAG GAGCCCTCCG TCCCGTCACA CTAGTGGCCT ACGAAAGGGT GGCAAAAGGA
1081  TCTGTCGTTA CGGTCGCTGG GGTGAGCTGA TTCGAGCTGA TCCCAAATCC TGAACTGGCA
1141  AAGAACCTGG TTACAGAATA CGGCCGATTT GACCCAGGAG CCATGAACTA CACAAAATTG
1201  ATACTGAGTG AGAGGGACCG TCTTGGCATC AAGACCGTCT GGCCGACAAG GGAGTACACT
1261  GACTTTCGCG AGTACTTCAT GGAGGTGGCC GACCTCAACT CTCCCCTGAA GATTGCAGGA
1321  GCA
```

OTHER PUBLICATIONS

Macreadie et al., "Passive protection against infectious bursal disease virus by viral VP2 expressed in yeast," Vaccine, vol. 8 Dec. 1990 (p. 549-552).*
Wang et al., "Identification of Neutralizatng Epitopes on the VP2 Protein of Infectious Bursal Disease Virus by Phage-Displayed Heptapeptide Library Screening and Synthetic Peptide Mapping," Viral Immunology, vol. 18, No. 3, 2005.*

Result 1 from us-11-170-056-5.rag.*

Result 2 from us-11-170-056-6.rng.*

Result 5 from us-11-170-056-6.rge.*

Hunt, "From gene to protein: a review of new and enabling technologies for multi-parallel protein expression," Protein Expression and Purification, 40 (2005) 1-22.*

Muller et al., "Research on infectious bursal disease—the past, the present and the future," Veterinary Microbiology 97 (2003) 153-165.*

Rodriguez-Chavez et al., "Characterization of the antigenic, immunogenic, and pathogenic variation of infectious bursal disease virus due to propogation in different host systems (bursa, embryo and cell culture). I. Antigenicity and Immunogenicity," Avian Pathology 2002, 31, 463-71.*

Muller et al., "Research on infectious bursal disease-the past, the present and the future," Veterinary Microbiology, 97, pp. 153-165 (2003).*

Azad, A.A., Jagadish, M.N., Brown, M.A., et al., 1987, Deletion mapping and expression in *Escherichia coli* of the large genomic segment of a birnavirus, *Virology* 161 (1): 145-152.

Brandt, M., Yao, K., Liu, M., Heckert, R.A. and Vakharia, V.N., 2001, Molecular determinants of virulence, cell tropism, and pathogenic phenotype of infectious bursal disease virus, *J. Virol.* 75, pp. 11974-11982.

Chalfie, M., Tu, Y., Euskirchen, G., Ward, W. W., Prasher, D. C. 1994. Green fluorescent protein as a marker for gene expression. *Science* 263: 802-805.

Crameri, A., Whitehorn, E. A., Tate, E., Stemmer, W. P. C., 1996, Improved green fluorescent protein by molecular evolution using DNA shuffling. *Nature Biotechnol.* 14: 315-319.

Dobos, P., Hill, B.J., Hallett, R., Kells, D.T., Becht, H., and Teninges, D., 1979 Biophysical and biochemical characterization of five animal viruses with bisegmented double-stranded RNA genomes, *J. Virol.* 32, pp. 593-605.

Fernandez-Arias, A., Risco, C., Martinez, S., Albar, J.P., Rodriguez, J.F. 1998 Expression of ORF A1 of infectious bursal disease virus results in the formation of virus-like particles. *J. Gen Virol.* 79:1047-54.

Frank, M.B., 1998 Insect Cell Culture & Baculovirus Infections. *In: Molecular Biology Protocols.* (http://omrf.ouhsc.edu/~frank/baculpro.html).

Hu, Y.C., Bentley, W.E., Edwards, G.H., Vakharia, V.N. 1999 Chimeric infectious bursal disease virus-like particles expressed in insect cells and purified by immobilized metal affinity chromatography. *Biotechnol Bioeng.* 63:721-729.

Hudson, P.J., McKern, N.M., Power, B.E. and Azad, .A.A., 1986 Genomic structure of the large RNA segment of infectious bursal disease virus, *Nucleic Acids Res.* 14, pp. 5001-5012.

Kibenge, F. S. B., Dhillon, A.S., Russell, R.G., 1988, Biochemistry and immunology of infectious bursal disease virus, *Journal of General Virology* 69: 1757-1775.

Kibenge, F.S., Qian, B., Nagy E., Cleghorn, J.R., Wadowska, D. Formation of virus-like particles when the polyprotein gene (segment A) of infectious bursal disease virus is expressed in insect cells. *Can J. Vet Res.* 1999, 63(1):49-55 (abstract).

Lombardo, E., Maraver, A., Caston, J.R., Rivera, J., Fernandez-Arias, A., Serrano, A., Carrascosa, J.L., Rodriguez, J.F. VP1, the putative RNA-dependant RNA polymerase of infectious bursal disease virus, forms complexes with the capsid protein VP3, leading to efficient encapsidation into virus-like particles. *J. Virol.* 1999, 73(8) 6973-83.

Maeda, S., Kawai, T., Obinata, M., Fujiwara, H., Horiuchi, T., Saeki, Y., Sato, Y., Furusawa, M. 1985. Production of human .alpha.-interferon in silkworm using a baculovirus vector. *Nature* 315: 592-594.

Martinez-Torrecuadrada, J.L., Caston, J.R., Castro, M., Carrascosa, J.L., Rodriguez, J.F., Casal, J.I. 2000 Different architectures in the assembly of infectious bursal disease virus capsid proteins expressed in insect cells. *Virology*. 278:322-331.

Marumoto, Y., Sato, Y., Fujiwara, H., Sakano, K., Sakei, Y., Agata, M., Furusawa, M., Maeda, S. 1987. Hyperproduction of polyhedrin-IGF II fusion protein in silkworm *larvae* infected with recombinant *Bombyx mori* nuclear polyhedrus virus. *J. Gen. Virol.* 68: 2599-2606.

Medin, J. A., Hung, L., Gathy, K., Evans, R. K., Coleman, M. S. 1990. Efficient, low-cost protein factories: expression of human adenosine deaminase in baculovirus-infected insect *larvae. Proc. Nat. Acad. Sci. USA* 87: 2760-2764.

Miyajima, A., Schreurs, J., Otsu, K., Kondo, A., Arai, K., Maeda, S., 1987, Use of silkworm, *Bombyx mori*, and an insect baculovirus vector for high-level expression and secretion of biologically active mouse interleukin-3, *Gene* 58: 273-281.

Muller, H. and Becht, H. 1982, Biosynthesis of virus-specific proteins in cells infected with infectious bursal disease virus and their significance as structural elements for infectious virus and incomplete particles, *Journal of Virology* 44 (1): 384-392.

Mundt, E., and V. N. Vakharia, V.N., 1996, Synthetic transcripts of double-stranded birnavirus genome are infectious. *Proc. Natl. Acad. Sci. USA* 93:11131-11136.

Prasher, D. C., Echenrode, V. K., Ward, W. W., Prendergast, F. G., Cormier, M. J, 1992, Primary structure of the *Aequorea victoria* green-fluorescent protein, *Gene*, 111:229-233.

Robertson, B.H., Morgan, D.O., Moore, D.M. 1984, Location of neutralizing epitopes defined by monoclonal antibodies generated against the outer capsid polypeptide, vp1, of foot-and-mouth-disease virus-a12, *Virus Research* 1 (6): 489-500.

Sanger, F., Nicklen, S.and Coulson, A.R., 1977, DNA sequencing with chain-terminating inhibitors, *Proc. Natl. Acad. Sci. U.S.A.* 74: pp. 5463-5467.

Shimomura, O., Johnson, F. H., Saiga, Y. 1962. Extraction, purification and properties of aequorin, a bioluminescent protein from the luminous hydromedusan. Aequorea. *J. Cell. Comp. Physiol.* 59: 223-227.

Snyder, D.B., Vakharia, V.N., Savage, P.K., 1992, Naturally occurring-neutralizing monoclonal-antibody escape variants define the epidemiology of infectious bursal disease viruses in the United States, *Arch. Virol.* 127: 89-101.

Snyder, D.B., Vakharia, V.N., Mengel-Whereat, S.A., et al., 1994, Active cross-protection induced by a recombinant baculovirus expressing chimeric infectious bursal disease virus structural proteins, *Avian Diseases* 38 (4): 701-707.

Vakharia, V.N. 1997, Biotechnology Annual Review vol. 3, 151-168.

Vakharia, V.N., Snyder, D.B., He, J., Edwards, G.H., Savage, P.K., and Mengel-Whereat, S.A., 1993, Infectious bursal disease virus structural proteins expressed in a baculovirus recombinant confer protection in chickens, *J. Gen. Virol.* 74, pp. 1201-1206.

Banda, A., Et Al., Molecular Characterization of Infectious Bursal Disease Virus from Commercial Poultry in the United States and Latin Ame, Avian Diseases, Jan. 2003, pp. 87-95, vol. 47, No. 1.

Dormitorio, T.V., Et Al., Sequence comparisons of the variable VP2 region of eight infectious bursal disease virus isolates, Avian Diseases, 1997, pp. 36-44, vol. 41, No. 1.

Ramadass, P., Et Al., Sequence analysis of infectious bursal disease virus Isolates from India: Phylogenetic relationships. Acta Virologica, 2003, pp. 131-135, vol. 47, No. 3.

* cited by examiner

```
1    ATGACAAACC TGCAAGATCA AACCCAACAG ATTGTTCCGT TCATACGGAG CCTTCTGATG
61   CCAACAACCG GACCGGCGTC CATTCCGGAC GACACCCTGG AGAAGCACAC TCTCAGGTCA
121  GAGACCTCGA CCTACAATTT GACTGTGGGG GACACAGGGT CAGGGCTAAT TGTCTTTTTC
181  CCTGGATTCC CTGGCTTCAAT TGTGGGTGCT CACTACACAC TGCAGAGCAA TGGAACTAC
241  AAGTTCGATC AGATGCTCCT GACTGCCCAG AACCTACCTG CCAGCTACAA CTACTGCAGG
301  CTAGTGAGTC GGAGTCTCAC AGTAAGGTCA AGCACACTCC CTGGTGGCGT TTATGCACTA
361  AACGGCACCA TAAACGCCGT GACCTTCCAA GGAAGCCTGA GTGAACTGAC AGATGTTAGC
421  TACAATGGAT TGATGTCTGC GACAGCCAAC ATTAACGACA AAATTGGGAA CGTCCTAGTA
481  GGGAAGGGG TAACCGTCCT CAGCTTACCC ACATCATATG ATCTTGGGTA TGTGAGGCTT
541  GGCGACCCCA TACCTGCTAT AGGGCTTGAC CCAAAAATGG TAGCAACATG TGACAGCAGT
601  GACAGGCCCA GAGTCTACAC CATAACCGCA GCCGATAATT ACCAATTCTC ATCACAGTAC
661  CAAACAGGCG GGGTAACAAT CACACTGTTC TCAGCCAACA TTGATGCCAT CACAAGTCTC
721  AGTGTTGGGG GAGAGCTCGT GTTCAAAACA AGCGTCCAAA GCCTTGTACT GGGCGCCACC
781  ATCTACCTTA TAGGCTTTGA TGGGACTGCG GTGATCACCA GAGCTGTGGC AACCAATGAA
841  GGGCTGACGG CCGGCATCGA CAATCTTATG CCATTCAATC TTGTGATTCC TAATGGTCAG
901  ATAACCCAGC CAATCACATC CATCAAACTG GAGATAGTGA CCTCCAAAAG CCATGGTGGC
961  GAGGGGGACC AGATGTCATG GTCGGCGAGT GGGAGCCTAG CAGTGACGAT GCAAAAGGA
1021 AACTATCCAG GAGCCCTCCG TCCCGTCACA CTAGTGGCCT ACGAAAGGGT GGCAAAAGGA
1081 TCTGTCGTTA CGGTCGCTGG GGTGAGCAAC TTCGAGCTGA TCCCAAATCC TGAACTGGCA
1141 AAGAACCTGG TTACAGAATA CGGCCGATTT GACCCCAGGAG CCATGAACTA CACAAAATTG
1201 ATACTGAGTG AGAGGGACCG TCTTGGCATC AAGACCGTCT GGCCGACAAG GGAGTACACT
1261 GACTTTCGCG AGTACTTCAT GGAGGTGGCC GACCTCAACT CTCCCCTGAA GATTGCAGGA
1321 GCA
```

Figure 1

MTNLQDQTQQIVPFIRSLLMPTTGPASIPDDTLEKHTLRSETSTYNLTVG

DTGSGLIVFFPGFPGSIVGAHYTLQSNGNYKFDQMLLTAQNLPASYNYCR

LVSRSLTVRSSTLPGGVYALNGTINAVTFQGSLSELTDVSYNGLMSATAN

INDKIGNVLVGEGVTVLSLPTSYDLGYVRLGDPIPAIGLDPKMVATCDSS

DRPRVYTITAADNYQFSSQYQTGGVTITLFSANIDAITSLSVGGELVFKT

SVQSLVLGATIYLIGFDGTAVITRAVAANNGETAGIDNLMPFNLVIPTNE

ITQPITSIKLEIVTSKSNGQEGDQMSWSASGSLAVTIHGGNYPGALRPVT

LVAYERVAKGSVVTVAGVSNFELIPNPELAKNLVTEYGRFDPGAMNYTKL

ILSERDRLGIKTVWPTREYTDFREYFMEVADLNSPLKIAGA

Figure 2

```
GA var.   MTNLQDQTQQIVPFIRSLLMPTTGPASIPDDTLEKHTLRSETSTYNLTVG    50
EDELVP2   MTNLQDQTQQIVPFIRSLLMPTTGPASIPDDTLEKHTLRSETSTYNLTVG    50
GLSVP2    MTNLQDQTQQIVPFIRSELMPTTFPASIPDDTLEKHTLRSETSTYNLTVG    50
          **************************************************

GA var.   DTGSGLIVFFPGFPGSIVGAHYTLQSNGNYKFDQMLLTAQNLPASYNYCR   100
EDELVP2   DTGSGLIVFFPGFPGSIVGAHYTLQSNGNYKFDQMLLTAQNLPASYNYCR   100
GLSVP2    DTGSGLIVFFPGFPGSIVGAHYTLQSNGNYKFDQMLLTAQNLPASYNYCR   100
          **************************************************

GA var.   LVSRSLTVRSSTLPGGVYALNGTINAVTFQGSLSELTDVSYNGLMSATAN   150
EDELVP2   LVSRSLTVRSSTLPGGVYALNGTINAVTFQGSLSELTDVSYNGLMSATAN   150
GLSVP2    LVSRSLTVRSSTLPGGVYALNGTINAVTFQGSLSELTDVSYNGLMSATAN   150
          **************************************************

GA var.   INDKIGNVLVGEGVTVLSLPTSYDLGYVRLGDPIPAIGLDPKMVATCDSS   200
EDELVP2   INDKIGNVLVGEGVTVLSLPTSYDZGYVRLGDPIPAIGLDPKMVATCDSS   200
GLSVP2    INDKIGNVLVGEGVTVESLPTSYDLGYVRLGDPIPAIGLDPKMVATCDSS   200
          **************************************************

GA var.   DRPRVYTITAADNYQFSSQYQTGGVTITLFSANIDAITSLSVGGELVFKT   250
EDELVP2   DRPRVYTITAADNYQFSSQYQTGGVTITLFSANIDAITSLSVGGELVFKT   250
GLSVP2    DRPRVYTITAADDYQFSSQYQTGGVTITLFSANIDAITSLSVGGELVFKT   250
          ************_*************************************

GA var.   SVQSLVLGATIYLIGFDGTAVITRAVAANNGETAGIDNLMPFNLVIPTNE   300
EDELVP2   SVQSLVLGATIYLIGFDGTAVITRAVAANNGLTAGIDNLMPFNLVIPTNE   300
GLSVP2    SVHSLVLGATIYLIGFDGSAVITRAVAaNNGLTTGTDNLMPFNLVIPTNE   300
          **_***************_***********_*_*****************

GA var.   ITQPITSIKLEIVTSKSNGQEGDQMSWSASGSLAVTIHGGNYPGALRPVT   350
EDELVP2   ITQPITSIKLEIVTSKSDGQAGEQMSWSASGSLAVTIHGGNYPGALRPVT   350
GLSVP2    ITQPITSIKLEIVTSKSGGQEGDQMSWSASGSLAVTIHGGNYPGALRPVT   350
          *****************_**_*_***************************

GA var.   LVAYERVAKGSVVTVAGVSNFELIPNPELAKNLVTEYGRFDPGAMNYTKL   400
EDELVP2   LVAYERVATGSVVTVAGVSNFELIPNPELAKNLVTEYGRFDPGAMNYTKL   400
GLSVP2    LVAYERVATGSVVTVAGVSNFELIPNPELAKNLVTEYGRFDPGAMNYTKL   400
          ********_*****************************************

GA var.   ILSERDRLGIKTVWPTREYTDFREYFMEVADLNSPLKIAGAFGFKDIIRA   450
EDELVP2   ILSERDRLGIKTVWPTREYTDFREYFMEVADLNSPLKIAGAFGFKDIIRA   450
GLSVP2    ILSERDRLGIKTWJPTREYTDFREYFMEVADLSSPLKIAGAFGFKDIIRA   450
          ************_********************_****************

GA var.   IRRIAVPVVSTLFPPAAPLAHAI    473
EDELVP2   IRRIAVPWSTLFPPAAPVAHAI     473
GLSVP2    IR---------------------    452
          **
```

Figure 3

INFECTIOUS BURSAL DISEASE VIRUS (IBDV) VARIANT FROM GEORGIA

CROSS REFERENCE TO RELATED APPLICATION

This application claims priority from U.S. Provisional Patent Application Nos. 60/634,186 filed on Dec. 8, 2004 in the name of Vikram N. Vakharia for "AN INFECTIOUS BURSAL DISEASE VIRUS (IBDV) VARIANT FROM GEORGIA" the contents of which are incorporated by reference herein for all purposes.

BACKGROUND OF THE INVENTION

1. Field of the Invention

The present invention relates to an infectious bursal disease virus (IBDV) strain comprising a variant structural protein VP2 that can be used to provide protection against a virulent challenge by classic and variant strains of IBDV.

2. Description of the Related Art

Infectious bursal disease virus (IBDV), a member of the Birnaviridae family, is the causative agent of a highly immunosuppressive disease in young chickens (Kibenge et al., 1988). Infectious bursal disease (IBD) or Gumboro disease is characterized by the destruction of lymphoid follicles in the bursa of Fabricius. In a fully susceptible chicken flock of 3-6 weeks of age the clinical disease causes severe immunosuppression, and is responsible for losses due to impaired growth, decreased feed efficiency, and death. Susceptible chickens less than 3 weeks old do not exhibit outward clinical signs of the disease but have a marked infection characterized by gross lesions of the bursa.

IBDV is a pathogen of major economic importance to the nation and world's poultry industries. It causes severe immunodeficiency in young chickens by destruction of precursors of antibody-production B cells in the bursa of Fabricius. Immunosuppression causes increased susceptibility to other diseases, and interferes with effective vaccination against Newcastle disease, Marek's disease and infectious bronchitis disease viruses.

The capsid of the IBDV virion consists of several structural proteins. As many as nine structural proteins have been reported but there is evidence that some of these may have a precursor-product relationship. The designation and approximately molecular weights of the viral proteins (VP) are as shown below.

| Viral Protein | Molecular Weight |
| --- | --- |
| VP1 | 90 kDa |
| VP2 | 41 kDa |
| VP3 | 32 kDa |
| VP4 | 28 kDa |
| VP5 (NS) | 17 kDa |

The IBDV genome consists of two segments of double-stranded (ds) RNA that vary between 2827 (segment B) to 3261 (segment A) nucleotide base pairs. The larger segment A encodes a 110-kDa precursor protein in a single large open reading frame (polyprotein ORF) which is cleaved by autoproteolysis to form the mature viral proteins VP2, VP3 and VP4 (Hudson et al., 1986). VP2 and VP3 are the major structural proteins of the virion. VP2 is the major host-protective immunogen of IBDV, and contains the antigenic regions responsible for the induction of neutralizing antibodies (Azad et al., 1987). A second open reading frame (ORF) encodes a protein (VP5), a 15-17 kDa arginine-rich nonstructural protein (NS), which precedes and partially overlaps the major polyprotein ORF. Although this protein is not present in the virion, it is detected in infected cells. The genomic segment B encodes VP1, a 90-kDa minor internal protein, which is the virion-associated RNA-dependent RNA polymerase In U.S. Pat. No. 6,231,868, the present inventor showed that the NS protein of IBDV (VP5) plays a role in viral pathogenesis by constructing a cDNA clone of IBDV segment A, wherein the initiation codon of the NS gene was mutated to a stop codon. Using the reverse genetics system, a wild-type IBDV was generated, as well as a mutant IBDV that lacked the expression of the NS protein. The properties of the recovered wild-type IBDV and mutant IBDV in cell culture were compared and their pathological function in the natural host evaluated. It was shown that the mutated IBDV, that lacked the expression of the NS protein, was less pathogenic than the wild type and that there was significant reduction in damage to the bursa of Fabricius.

It has been demonstrated that the VP2 protein is the major host protective immunogen of IBDV, and that it contains the antigenic region responsible for the induction of neutralizing antibodies. This region containing the neutralization site has been shown to be highly conformation-dependent. The VP3 protein has been considered a group-specific antigen because it is recognized by monoclonal antibodies directed against it from strains of both serotype I and II viruses. The VP4 protein appears to be a virus-coded protease that is involved in the processing of a precursor polyprotein of the VP2, VP3 proteins.

In the past, control of IBDV infection in young chickens has been achieved by live vaccination with avirulent strains, or principally by the transfer of maternal antibody induced by the administration of live and killed IBDV vaccines to breeder hens. Unfortunately, in recent years, virulent variant strains of IBDV have been isolated from vaccinated flocks in the United States. The use of a select panel of monoclonal antibodies (Mabs), raised against various strains of IBDV, has led to the identification of naturally occurring GLS, DS326, RS593 and Delaware variant viruses in the United States. Substantial economic losses have been sustained due to the emergence of these antigenic variants. These variant strains are antigenically different from the classic strains of IBDV most typically isolated before 1985, and lack epitope(s) defined by neutralizing Mabs B69 and R63 (Snyder et al., 1988a; Snyder et al., 1988b; Snyder et al., 1992). Since the appearance of these variant strains in the field, many commercially available live and killed vaccines for IBDV have been reformulated in an attempt to better match the greater antigenic spectrum of viruses recognized to be circulating in the field. For example, some companies have developed individual vaccines against GLS and Delaware strains of IBDV that are characterized by their reactivity with neutralizing Mabs 57 and 67, respectively.

Thus, it would be advantageous to develop a vaccine comprising a structural antigenic viral protein, which provides wider protection for multiple strains of IBDV by inducing antibody production directed at different strains of IBDV.

SUMMARY OF THE INVENTION

In one aspect, the present invention relates to a variant IBDV strain comprising a VP2 gene encoding for variant protein comprising amino acid residues of SEQ ID NO. 5.

In another aspect, the present invention provides for recombinant genetic information comprising a nucleotide sequence corresponding to a variant VP2 gene (SEQ. ID NO. 6) for insertion into an expression vector, wherein the expression vector includes at least one copy of the nucleotide sequence.

In yet another aspect, the present invention relates to an infectious bursal disease virus strain comprising a VP2 protein encoded by a nucleotide sequence selected from the group consisting of
  (a) a nucleic acid sequence that has more than 97% identity to SEQ ID NO 6; and
  (b) a nucleic acid sequence fully complementary to a nucleic acid of (a); and wherein the expressed VP2 protein induces antibodies against multiple variant strains of IBDV.

In a still further aspect, the present invention provides for a recombinant baculovirus comprising at least a VP2 gene (SEQ ID NO: 6) and optionally a VP3 gene for introduction into an insect cell for expression of the variant VP2 protein (SEQ ID NO. 5)

The present invention further relates to a sub-unit vaccine to reduce and/or prevent infection by IBDV, the sub-unit vaccine comprising structural protein variant VP2 (SEQ ID NO 5).

In yet another aspect, the present invention relates to sub-unit vaccine to reduce and/or prevent infection by IBDV, the sub-unit vaccine comprising structural protein variant VP2 (SEQ ID NO 5) and a VP3 structural protein folded as an empty IBDV viral capsid. The vaccine may further comprise a reporter protein co-expressed with the IBDV structural proteins. The VP3 protein may be from any IBDV strain, known to those skilled in the art, including but not limited to classic, GLS, Delaware, D78 and AL2 strains. Sequence information is available from Genebank relating to segment A and segment B genes, including VP3 genes from different IBDV strains.

In another aspect, the variant VP2 protein is expressed by a process, comprising the steps of:
  inserting nucleotide sequences encoding for at least the variant VP2 protein into an expression vector, wherein the nucleotide sequence is selected from the group consisting of:
    (a) a nucleic acid sequence that has more than 97% identity to SEQ ID NO 6; and
    (b) a nucleic acid sequence fully complementary to a nucleic acid of (a); and
    wherein the expressed VP2 protein induces antibodies against multiple variant strains of IBDV;
  transfecting the expressing vector into a host cell and maintaining suitable condition for expressing the variant VP2 protein; and
  recovering VP2 protein.

In yet another aspect, the present invention relates to a method of generating structural proteins of IBDV assembled as an empty viral capsid comprising the steps of:
  (a) providing a recombinant baculovirus comprising a polynucleotide encoding IBDV Consisting of VP2,-VP4-VP3 from a single native virus, and a reporter protein, wherein the nucleotide sequence for encoding VP2 is SEQ ID NO: 6;
  (b) infecting insect larvae with the recombinant baculovirus; and
  (c) maintaining suitable conditions for expression of IBDV Segment A proteins VP2,-VP4-VP3 to generate structural proteins VP2 and VP3 assembled as an empty IBDV capsid; and
  (d) recovering the empty IBDV capsid from the larvae, wherein the empty IBDV capsid approximates the size and conformation of the native IBDV.

In yet another aspect, the present invention relates to production of IBD virus-like particles having the structural conformation of native IBDV but without the RNA genome, wherein the virus like particles comprises VP2 of SEQ ID NO: 5 and VP3.

Another aspect of the present invention relates to a broad spectrum IBD poultry vaccine that comprises a poultry protecting amount of the recombinant vector described above; and a physiologically acceptable carrier.

A still further aspect of the present invention relates to a live, nonpathogenic Georgia variant IBDV strain and method of producing same for use as a vaccine to protect against IBDV, the method comprising the following steps:
  (a) preparing at least one cDNA of infectious bursal disease virus genome segments A and B, wherein the segment A comprises a VP2 gene of SEQ ID NO 1 or 6 and is modified to prevent expression of NS protein;
  (b) transcribing said cDNA to produce synthetic RNA transcripts,
  (c) transfecting host cells with said synthetic RNA transcripts,
  (d) incubating said host cells in a culture medium, and
  (e) isolating live, nonpathogenic, infectious bursal disease virus from said culture medium.

This method may include cDNA that contains epitopic determinants from at least two different strains of infectious bursal disease virus, including the Georgia variant VP2 gene of the present invention and a VP3 gene from another strain, or Segment A from the Georgia variant IBDV strain of the present invention and a Segment B from a different strain.

Other aspects and features of the invention will be more fully apparent from the ensuing disclosure and appended claims.

BRIEF DESCRIPTION OF THE FIGURES

FIG. 1 shows the nucleotide sequence of the VP2 gene of the Georgia strain of IBDV (SEQ ID NO: 6).

FIG. 2 shows the amino acid sequence of the VP2 protein of the Georgia strain of IBDV (SEQ ID NO: 5).

FIG. 3 shows the difference of the amino acid residues for VP2 Protein between U.S. GLS-5 and E/DEL variants, and the Georgia strain of the present invention. Notably, a precursor or primer was used in the consensus region of pVP2 gene for amplification and hence the deduced sequence is 473 amino acids long (SEQ ID NO: 2) and the variant VP2 protein is the first 441 amino acid residues. SEQ ID NO: 1 encodes for such protein with precursor.

DETAILED DESCRIPTION OF THE INVENTION

The present invention is based on the discovery of a variant structural protein VP2 from a variant strain of Infectious Bursal Disease Virus (IBDV) with that can be used in a vaccine either as a live, nonpathogenic vaccine or as a sub-unit vaccine either alone or in combination with VP3, assembled as an empty viral capsid that can be administered as effective sub-unit vaccines to reduce and/or prevent infection by IBDV.

This variant IBD virus strain from Georgia has the characteristics of both "GLS" and "Delaware" strains of IBDV, which is characterized by the reactivity with neutralizing Mabs 57 and 67. Thus, the use of this single sub-unit vaccine comprising the Georgia variant VP2 protein has the ability to reduce or prevent infection by not only the Georgia strain but also the GLS, Delaware, D78 and AL2 strains.

"Sub-unit vaccine" as used herein is defined as a vaccine including sub viral components that are post-translationally modified and correctly folded to act as immunogens.

"Virus-like particle" as used herein is defined as a virion that lacks genetic material with 3D structure and size of a native virus.

"Nucleotide sequence" as used herein is defined as a sequence of nucleotides connected by phosphodiester linkages. Nucleotide sequences are presented herein in the direction from the 5' to the 3' direction and can be a deoxyribonucleic acid (DNA) molecule or ribonucleic acid (RNA) molecule.

"Epitopic determinant" as used herein is defined as an amino acid sequence which correspond to an epitope recognized by one or more monoclonal antibodies.

"Reporter gene" as used herein is defined as a gene that expresses a reporter protein, which causes some determinable characteristic in a recombinant system simultaneously with the expression of the subject gene to indicate the expression of that other gene.

Expression of at least the Georgia variant VP2 and preferably also VP4-VP3 leads to the production of virus-like particles formed by the self-assembly of pVP2 and VP3. A cDNA clone of segment A of the IBDV consisting of a nucleotide sequence encoding for structural proteins VP2 and VP3 and a non-structural protein VP4; and optionally a reporter gene is constructed in tandem so that the IBDV structural proteins and reporter protein are expressed simultaneously. U.S. Patent Application No. 2003/0072772, the contents of which are incorporated herein, provides guidance for generating such virus-like particles.

Briefly, the cDNA clone containing the preferred coding and/or non-coding regions of IBDV-RNA segment A can be prepared using standard cloning procedures and methods, as described for IBDV in Mundt, E., 1996, the contents of which are hereby incorporated herein by reference for all purposes. Manipulations of DNAs can be performed according to standard protocols (Sambrook, J., 1989).

To generate cDNA clones of a coding region of the desired structural proteins, the genomic RNA is used as a template for synthesizing and amplifying according to general RT-PCR techniques well known in the art. Specifically, U.S. Pat. No. 5,595,912 provides techniques applicable for cDNA amplifying in the present invention. The desired amplified fragments are then cloned into an expression vector.

Useful vectors for this purpose include plasmids, and viruses such as baculoviruses, herpes virus (HVT) and pox viruses, e.g., fowl pox virus, and the like. The vectors may also expression control sequences including, but not limited to, a promoter, enhancers, operators, inducers, ribosome binding sites, etc.

A promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. Those promoters most commonly used in recombinant DNA construction include the beta.-lactamase (penicillinase) and lactose promoter systems and a tryptophan (TRP) promoter system. While these are the most commonly used, other microbial promoters have been discovered and utilized, and details concerning their nucleotide sequences have been published, enabling a skilled worker to introduce functional promoters into plasmid vectors.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

Also provided herein is a host cell transformed with the recombinant vector of the present invention or a host cell transfected with the synthetic RNA of the present invention. The host cell may be a eukaryotic or a prokaryotic host cell. Suitable examples are E. coli, insect cell lines such as Sf-9, chicken embryo fibroblast (CEF) cells, chicken embryo kidney (CEK) cells, African green monkey Vero cells and the like. Further, the host cell can be insect cell that is transfected for expression of the desired protein(s).

Means of transforming or transfecting cells with exogenous polynucleotide such as DNA molecules are well known in the art and include techniques such as calcium-phosphate-or DEAE-dextran-mediated transfection, protoplast fusion, electroporation, liposome mediated transfection, direct microinjection and adenovirus infection.

The most widely used method is transfection mediated by either calcium phosphate or DEAE-dextran. Although the mechanism remains obscure, it is believed that the transfected DNA enters the cytoplasm of the cell by endocytosis and is transported to the nucleus. Depending on the cell type, up to 90% of a population of cultured cells can be transfected at any one time. Because of its high efficiency, transfection mediated by calcium phosphate or DEAE-dextran is the method of choice for experiments that require transient expression of the foreign DNA in large numbers of cells. Calcium phosphate-mediated transfection is also used to establish cell lines that integrate copies of the foreign DNA, which are usually arranged in head-to-tail tandem arrays into the host cell genome.

Electroporation can be extremely efficient and can be used both for transient expression of cloned genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA. The application of brief, high-voltage electric pulses to a variety of mammalian and plant cells leads to the formation of nanometer-sized pores in the plasma membrane. DNA is taken directly into the cell cytoplasm either through these pores or as a consequence of the redistribution of membrane components that accompanies closure of the pores.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, E. coli can be transformed using pBR322, a plasmid derived from an E. coli species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own polypeptides.

In yet another embodiment, the present invention contemplates a process of preparing a live IBDV of the present invention comprising transfecting cells with a polynucleotide that encodes for the Segment A and B and comprising the variant VP2 sequence to produce transformed host cells; and maintaining the transformed host cells under biological conditions sufficient for expression of the virus. The transformed host cells can be eukaryotic cells or prokaryotic cells. Most preferably, transfection is accomplished using a hereinbefore disclosed expression vector. A variety of cells are amenable to a process of the invention, for instance, yeasts cells, human cell lines, and other eukaryotic cell lines known well to those of the art.

Also part of this invention is an NS protein deficient IBDV vaccine comprising a protecting amount of a recombinantly produced virus or portion of a virus, wherein the virus does not induce pathological lesions. A cDNA clone of IBDV segment A is constructed, in which the first and only initiation codon (ATG) of NS protein A is mutated to a stop codon (TAG).

The virus can be further modified or inactivated by chemical or physical means. Chemical inactivation can be achieved by treating the virus with, for example, enzymes, formaldehyde, .beta.-propiolactone, ethylene-imine or a derivative thereof, an organic solvent (e.g. halogenated hydrocarbon) and or a detergent. If necessary, the inactivating substance can be neutralized after the virus has been inactivated. Physical inactivation can be carried out by subjecting the viruses to radiation such as UV light, X-radiation, or y-radiation.

The virus can also be modified by known methods including serial passage, deleting further sequences of nucleic acids and site directed. mutagenesis either before or after production of the infectious virus.

The virus can be a chimeric recombinant virus which contains epitopic determinants for more than one strain of IBDV. Epitopic determinants as discussed in the present document are amino acids or amino acid sequences which correspond to epitopes recognized by one or more monoclonal antibodies. Since VP2 protein is the major host protective immunogen of IBDV, the chimeric virus must include at least a portion of the variant VP2 in addition to the modified NS gene according to the present invention. Methods for producing a chimeric virus are disclosed in Vakharia, 1997; Snyder et al., 1994 and WO 95/26196, the contents of which are incorporated by reference herein for all purposes.

Synthetic transcripts derived from cloned DNA corresponding to the entire genome of a segmented dsRNA animal virus have been demonstrated to give rise to a replicating virus as described in U.S. Pat. Nos. 5,871,744 and 6,231,868, the contents of which are incorporated by reference herein for all purposes.

Briefly, the recovery of infectious virus after transfecting cells with synthetic plus-sense RNAs derived from cloned cDNA of a virus with a dsRNA genome completes the quest of generating reverse infectious systems for RNA viruses. Transfection of cells with plus-sense RNAs of both segments is sufficient to generate infectious virus (IBDV).

Transfection of plus-sense RNAs from both segments into the same cell is necessary for the successful recovery of IBDV. Transfected RNAs of both segments has to be translated by the cellular translation machinery. The polyprotein of segment A is presumably processed into NS protease and VP2 and VP3 proteins, which form the viral capsid. The translated protein VP1 of segment B acts as a RNA-dependent RNA polymerase and transcribes minus-strands from synthetic plus-strands of both segments, and the reaction products form dsRNA.

To unequivocally prove that the infectious virus (IBDV) contained in supernatants of transfected cells is indeed derived from the synthetic transcripts, one recombinant virus may be generated containing sequence tags in segment B. Restriction enzyme digests of the RT-PCR products and sequence analysis of the cloned DNA fragments are used to verify the presence of these sequence tags in the genomic RNA segments.

The recovery of infectious virus (IBDV) demonstrates that only the plus-strand RNAs of both segments are required to initiate replication of dsRNA. In order to study the function of the 15-17 kDa nonstructural (NS) protein in viral growth and pathogenesis, a cDNA clone of IBDV segment A is constructed, in which the NS protein is mutated to prevent expression. Segment A is preferably mutated in more than one region to prevent the expression of NS protein. Mutation in more than one region of the NS protein is preferable to lower the chances of a reversion to the wild type strain.

Transfection of cells with combined transcripts of either modified or unmodified segment A along with segment B will produce viable IBD viruses. When transfectant viruses are characterized by immunofluorescence assays using NS-specific antiserum, a lack of NS protein expression is characterized by lack of a fluorescence signal. Furthermore, replication kinetics and cytotoxic effects of the mutant virus can be compared with that of the wild type (WT) virus in vitro. The mutant virus will exhibit decreased cytotoxic effects in cell culture.

To compare the immune response induced by the unmodified and mutated IBDV, chickens can be inoculated with the mutant and unmodified viruses, bled, and their sera analyzed by virus neutralization (VN) test. This assay will show that the mutant virus, which is deficient in producing NS protein, does not affect the immune response to IBDV in the natural host.

Following transfection, a transfected cell is maintained under culture conditions for a period of time sufficient for expression of the virus polypeptide. Culture conditions are well known in the art and include ionic composition and concentration, temperature, pH and the like. Typically, transfected cells are maintained under culture conditions in a culture medium. Suitable medium for various cell types are well known in the art. In a preferred embodiment, temperature is from about 20° C. to about 50° C., more preferably from about 30° C. to about 40° C. and, even more preferably about 37° C. pH is preferably from about a value of 6.0 to a value of about 8.0, more preferably from about a value of about 6.8 to a value of about 7.8 and, most preferably about 7.4. Other biological conditions needed for transfection and expression of an encoded protein are well known in the art.

A recombinant peptide is recovered or collected either from the transfected cells or the medium in which those cells are cultured. Recovery comprises isolating and purifying the recombinant polypeptide. Isolation and purification techniques for polypeptides are well known in the art and include such procedures as precipitation, filtration, chromatography, electrophoresis and the like. For instance, the immunogenic polypeptides can be harvested using conventional techniques described in Dobos et al., 1979.

These virus polypeptides can be used to prepare vaccines which will confer protection on inoculated poultry, in particular, chickens, and in a preferred embodiment, broiler chickens, protection against challenge from each IBDV bearing an epitope reflected in the plurality of epitopic determinants present in the inoculum. Thus, a single immunogen gives rise to immunity against a variety of IBDV strains while remaining non-pathogenic to poultry.

The administration of the vaccines can be effectively done according to well-established procedures. In U.S. Pat. No. 5,064,646, which is incorporated herein by reference, methods are described for the effective inoculation of chicks. Similar administration and dosage regimens can be employed herein. The vaccines may be prepared by simple incorporation in a pharmaceutical carrier, typically a suspension or mixture. Appropriate dosage values are best determined through routine trial and error techniques, given the different antibody titers induced and/or the quantity of different epitopes present which will induce complete cross-immunity to virulent challenge. In general, pharmacologically acceptable carriers such as a phosphate buffered saline, cell culture medium, Marek's virus vaccine diluent oil adjuvants and other adjuvants, etc., can be used. Administration is preferably done to hens entering egg-laying periods which provides induction of antibody which is passively transferred through the egg to the chick to prevent early infection by virulent field strength IBDV. Conversely, the recombinant vaccine may be delivered in a replicating vector at any time in a chicken's life span, preferably at one day of age. Experience has demonstrated that, generally, that the level of protection may be improved by a second inoculation.

Physiologically acceptable carriers for vaccination of poultry are known in the art and need not be further described herein. In addition to being physiologically acceptable to the poultry the carrier must not interfere with the immunological response elicited by the vaccine and/or with the expression of its polypeptide product.

Other additives, such as adjuvants and stabilizers, among others, may also be contained in the vaccine in amounts known in the art. Preferably, adjuvants such as aluminum hydroxide, aluminum phosphate, plant and animal oils, and the like, are administered with the vaccine in amounts sufficient to enhance the immune response to the IBDV. The amount of adjuvant added to the vaccine will vary depending on the nature of the adjuvant, generally ranging from about 0.1 to about 100 times the weight of the IBDV, preferably from about 1 to about 10 times the weight of the IBDV.

The vaccine of the present invention may also contain various stabilizers. Any suitable stabilizer can be used including carbohydrates such as sorbitol, mannitol, starch, sucrose, dextrin, or glucose; proteins such as albumin or casein; and buffers such as alkaline metal phosphate and the like. A stabilizer is particularly advantageous when a dry vaccine preparation is prepared by lyophilization.

The vaccine can be administered by any suitable known method of inoculating poultry including nasally, ophthalmically, by injection, in drinking water, in the feed, by exposure, and the like. Preferably, the vaccine is administered by mass administration techniques such as by placing the vaccine in drinking water or by spraying the animal' environment. When administered by injection, the vaccines are preferably administered parenterally. Parenteral administration as used herein means administration by intravenous, subcutaneous, intramuscular, or intraperitoneal injection. Preferably, the vaccine is injected in ovo to embryonated eggs, such as 14-18 day-old embryonated eggs.

The vaccine of the present invention is administered to poultry to prevent IBD anytime before or after hatching. Preferably, the vaccine is administered prior to the time of birth and after the animal is about 6 weeks of age. Poultry is defined to include but not be limited to chickens, roosters, hens, broilers, roasters, breeders, layers, turkeys and ducks.

Examples of pharmaceutically acceptable carriers are diluents and inert pharmaceutical carriers known in the art. Preferably, the carrier or diluent is one compatible with the administration of the vaccine by mass administration techniques. However, the carrier or diluent may also be compatible with other administration methods such as injection, eye drops, nose drops, and the like.

The present invention also comprises variant VP2 peptides that can be used for diagnostic purposes. For example, the variant VP2 protein antigens generated by the methods of the present invention can be used in an ELISA format to detect different strains of IBDV positive sera. Also, variant VP2 specific antibodies can be used to affinity purify the IBDV virus.

Also included within the scope of the present invention are nucleic acid sequences encoding a functional equivalent of the variant VP2 proteins having corresponding immunological characteristics. As is well known in the art, the degeneracy of the genetic code permits substitution of bases in a codon resulting in another codon but still coding for the same amino acid, e.g. the codon for the amino acid glutamic acid is both GAT and GAA. Consequently, it is clear that for the expression of a polypeptide with the amino acid sequence of variant VP2 can be made of a derivate nucleic acid sequence (functional equivalent) with such an alternative codon composition.

Introduction of the genes encoding the variant VP2 protein and optionally VP3 protein as envisioned in the present invention is ideally effected via a baculovirus that infect only insects. Baculoviruses that can be manipulated to incorporate DNA are commercially available. Construction of appropriate baculovirus vectors to express the subject proteins is apparent to one skilled in the art. The following text, which is incorporated herein by reference, is an example of a reference that provides sufficient information and instruction to enable construction of a suitable baculovirus vector: (O'Reilly et al., 1992). There are also commercial kits available that provide the necessary instructions and reagents for baculovirus vector construction.

The expression level of the subject proteins may be increased by the use of a polyhedrin negative baculovirus. In this virus, the gene encoding at least one of the subject proteins may be put under the polyhedrin promoter to boost the expression when compared to the other promoters. Preferably, the genes encoding the separate subject proteins are put under the control of separate promoters, such as polyhedrin and P10 promoters.

Generally baculovirus expression may be accomplished by the following protocol:

Ligating the gene of interest to a bacterial transfer vector. The inserts are typically flanked by portions of viral genes to permit homologous recombination with replication defective, linear, viral DNA. Verify direction of the inserts relative to the polyhedrin promoter and purify plasmids for transfection into insect cells.

Co-transfecting insect cells with the recombinant transfer vector. Electroporation, lipid, and calcium phosphate-mediated transformations work well. These recombination events insert your gene into the virus and complement defective viral gene(s) to permit viral replication. In some vectors, this may also generate production of marker proteins such as beta-galactosidase. Non-recombinant viruses are kept to a minimum with this system.

The optimal temperature for insect cell growth is 27° C. If an incubator is not available, the cells will grow at room temperature but at a slower rate. Cells may be grown in T-flasks or shaker flasks. Further discussion relating to optimal production of proteins using a baculovirus/insect system is described in Frank, 1998, the content of which is incorporated herein by reference.

Further, the recombinant baculovirus may also be used to infect insect larvae for the expression of the IBDV structural proteins and reporter proteins. As stated above, although mammalian and insect cell systems can be used to manufacture proteins, expensive and complex media are required and the bioreactors, in which the cells are grown, must be run for extended periods creating a risk of contamination of the cell culture. As such, the present invention contemplates infection of permissive insect larvae that can be infected with a baculovirus, and can be grown quickly and inexpensively. Additionally, yields can be obtained from insect larvae that cannot be obtained from cells and this fact makes insect larvae an appealing alternative to cell based protein manufacturing.

To effect infection, once a recombinant baculovirus has been constructed, a solution containing the recombinant baculovirus may be sprayed on the larvae's food for absorption therein or the baculovirus can be injected directly into the hemocoel of the larvae.

Because foreign proteins have been expressed in a variety of insect larvae; Bombyx mori, the silkworm (Maeda et al., 1985; Miyajima, et al., 1987), Trichoplusia ni, the cabbage looper larvae (Medin et al., 1990) and Manduca sexta, the tobacco hornworm (U.S. Pat. No. 5,471,858) there is a wide selection of insect larvae that could be utilized with this system. The larvae of the cabbage looper has been utilized and is typical of the ideal larvae envisioned for use in the present invention. Cabbage looper larvae can be ordered from commercial sources such as Entopath, Inc. (Easton, Pa.) and can be easily grown in a laboratory according to the instructions provided by the supplier. Media for the larvae can be made from alfalfa meal, pinto beans, Brewer's yeast, ascorbic acid, wheat germ, sorbic acid, vitamins, and antibiotics (aureomycin).

There is a balance to be struck as to the best stage in the larval cycle of the cabbage looper or any other suitable larvae to initiate baculovirus infection. The baculovirus kills the larvae after five days so there is a limited time in which they have to grow and express the subject protein. Because the size of the larvae is related to the amount of protein they express; small larvae produce insignificant amounts of protein, it is more effective to infect the larvae when they are larger. However, if the larvae are too large, too much baculovirus is required for infection. As such, Baculovirus infection in the fourth instar, which is the last instar prior to pupation, seems to strike the optimal balance between the larvae's size and the amount of virus required for infection.

A preferred embodiment of the present invention is a method that infects the larvae on a continuous basis and harvesting of the larvae from the production population when the reporter gene signals production of the structural proteins. A semi-continuous embodiment is also envisioned by the inventor wherein the larvae are infected at substantially the same time and then harvested individually when they express the reporter gene.

Consequently, the reporter gene of the present invention is capable of expression in insect larvae at the same time as the gene encoding the subject protein. The determinable characteristic is a change in appearance of the living larvae that can be easily visualized. Ideally, the characteristic is visible in normal light or other wavelengths of light. Thus, determination of the reporter gene's expression is simply accomplished by viewing the larvae under normal light conditions and other light conditions. Furthermore, the amount of the expressed reporter protein will directly correspond to the amount of the other protein, such as the desired structural proteins in the larvae. Consequently, the intensity of the effect created in the appearance of the living larvae by the amount of reporter protein can be used to directly measure the amount of subject protein actually present in each larvae.

An excellent choice for the role of the reporter gene is the green fluorescent protein (GFP) that was originally isolated from the jellyfish, Aequorea victoria, and was first described in 1962 (Shimomura et al., 1962). GFP emits bright green light when simply exposed to UV or blue light, unlike other bioluminescent reporters. The emission of green light is due to the transfer of energy from the photoprotein, aequorin, of the organism to GFP. The cDNA of GFP was cloned from Aequorea victoria in 1992 (Prasher et al., 1992). One such GFP is a 238 amino acid protein with a molecular weight of 28 kDa (Chalfie et al., 1994) having a major absorption peak at 395 nm and a minor peak at 470 nm with a single emission peak at 509 nm.

Advantageously, fluorescence of GFP is species-independent and requires no substrate, cofactor, or additional proteins for illuminating green light. Unlike other reporter tags such as luciferase, b-galactosidase, or fluorescent-tagged antibodies, GFP does not require fixation techniques that are toxic to the cells under the investigation.

Additionally, GFP mutations have also been developed that serve well in the capacity of the reporter gene. GFPuv was optimized for UV excitation (Crameri et al., 1996). GFPuv is 18 times brighter than wild-type GFP and can be easily detected by the naked eye when excited with standard, long-wave UV light (e.g., source for many DNA transilluminator light tables). This variant contains additional amino acid mutations which increases its translational efficiency. Purified GFPuv has the same excitation and emission maxima as wild-type GFP.

Mutants of GFP are available commercially and include variants with the blue and red-shifted proteins along with several that have various intensities of green for which the codon composition has been altered. Among the commercial vendors of these mutants are Life Technologies, Inc., Clontech, Inc., and Invitrogen, Inc.

It is envisioned that the present invention will include the use of an automated system for selecting individual larvae for harvest. A monitoring capability could be added to such a system by attaching an LED/detector to each fin where the larvae hang and wiring the LED/detector and a fin to a separate controller. When the LED/detector detects a sufficient intensity of the green color of the GFP expressed in a larva, a signal would be sent to the controller which in turn would deliver voltage to the fin where the transmitting LED/detector is located. The voltage would shock the larva causing it to fall off the fin into a collection receptacle. Another possible monitoring system could resemble the conveyor belt/switching gate apparatus used by dairy egg manufacturers, where the brightest larvae are harvested.

Although an automated system is preferable, since GFP mutants expressed in larvae, such as GFPuv, can be discerned by the human eye in normal laboratory light in larvae at least two or three days after infection with baculovirus and detection of GFP with human eyesight under UV light possible after at least three days, manual infection and selection for harvest is certainly feasible.

Conditions which enhance the expression of at least the variant VP2 and the reporter gene, particularly green fluorescent protein, include infection with a viral loading of at least $5\times10^7$ pfu/mL recombinant baculovirus, temperature of at least about 30° C., harvesting of the larvae at least 3-5 days, more particularly at least 4 days, after post infection; at a pH of at least about 3.5 to about 4.0 and in the presence of protease inhibitors such as PMSF, EDTA and benzamidine, preferably at least about 1.5 mM.

Preservation of the larvae after selection for harvest in the present invention is envisioned to be conducted by freezing the selected larvae and then homogenizing the larvae in conditions which minimize the activity of proteases.

The previously described versions of the present invention have many advantages including the easy selection of larvae at the point of their optimal protein expression. Because the visible expression of GFP will occur simultaneously with the expression of the IBDV structural proteins, each larvae can be selected for harvest when it is expressing the optimal amount of the subject protein. Furthermore, if the GFP is fused with at least one of the structural proteins, when expressed, it is possible in the present invention to quantify the amount of subject protein in an individual larvae. This in turn allows an estimation of the total yield from a production population to be made.

In addition, larvae which are not expressing significant amounts of the IBDV structural proteins can be removed from the production population so that resources are not expended attempting to purify the subject protein from them. Furthermore, because the larvae can be grown on inexpensive media, it is unnecessary to incur the high expense of formulating complex media and maintaining bioreactors.

The visualization of the reporter protein will permit the progress of the expression of at least the variant VP2 protein to be monitored through the purification process directly and indirectly. This will also serve to facilitate purification. Separation of the reporter protein from the VP2 variant protein and any other expressed structural proteins may be accomplished in several ways. For example, an affinity ligand could be engineered onto the reporter protein. The affinity ligand can be used to bind and separate the structural proteins from the larval extract during the initial purification.

As a further means to simply purification, the linkage between the gene for the VP2 peptide and the reporter gene could comprise a gene which expresses a protein that is cleaved by a specific enzyme. Once the fusion product is separated from the homogenate via the affinity ligand, it could be exposed to the enzyme which cleaves the linking protein to separate the subject protein and the reporter protein. Then, a one-step purification could be performed to purify the subject protein.

Once the VP 2 protein, VP2-VP4-VP-3, and/or VP2 and VP3 proteins are separated from the reporter protein, if it is determined that the GFP protein must be removed for effective vaccine, the purified protein or VLP is administered as a sub-unit vaccine to avian species.

It is contemplated by the inventors to include more than one strain of IBDV so that more than one type of empty viral capsid can be generated and recovered. Thus, the recovered empty viral capsids may contain epitopic determinants for more than one strain of IBDV.

Eukaryotic microbes, such as yeast can also be used for expression of the variant VP2 protein. *Saccharomyces cerevisiae* or common baker's yeast is the most commonly used among eukaryotic microorganisms, although a number of other strains are commonly available. For expression in Saccharomyces, the plasmid YRp7, for example, is commonly used. This plasmid already contains the trp1 gene, which provides a selection marker for a mutant strain of yeast lacking the ability to grow in tryptophan, for example ATCC No. 44076 or PEP4-1. The presence of the trp1 lesion as a characteristic of the yeast host cell genome then provides an effective environment for detecting transformation by growth in the absence of tryptophan. Suitable promoter sequences in yeast vectors include the promoters for 3-phosphoglycerate kinase or other glycolytic enzymes such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also introduced into the expression vector downstream from the sequences to be expressed to provide polyadenylation of the mRNA and termination. Other promoters, which have the additional advantage of transcription controlled by growth conditions are the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization. Any plasmid vector containing a yeast-compatible promoter, origin or replication and termination sequences is suitable. For example, the pESC-URA vector from Stratagene may be used, which has two promoters in the plasmid, and hence, it could be used for coexpressing two proteins simultaneously.

Antibodies or antiserum directed against the variant VP2 peptides according to the present invention have potential use in passive immunotherapy, diagnostic immunoassays and generation of antibodies.

Thus, in another aspect, the present invention contemplates a process of producing an antibody immunoreactive with the variant VP2 protein, comprising the steps of (a) transfecting recombinant host cells with polynucleotides that encode the variant VP2 peptide; (b) culturing the host cells under conditions sufficient for expression of the peptides; (c) recovering the peptides; and (d) preparing antibodies to the peptides.

Typically, a monoclonal antibody of the present invention can be readily prepared by a technique which involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine. This culturing provides a population of hybridomas from which specific hybridomas are selected. Typically, selection of hybridomas is performed by culturing the cells by single-clone dilution in microliter plates, followed by testing the individual clonal supernatants for reactivity with an antigen-polypeptides. The selected clones can then be propagated indefinitely to provide the monoclonal antibody.

By way of specific example, to produce an antibody of the present invention, mice are injected intraperitoneally with between about 1-200 µg of an antigen comprising a polypeptide of the present invention. B lymphocyte cells are stimulated to grow by injecting the antigen in association with an adjuvant such as complete Freund's adjuvant (a non-specific stimulator of the immune response containing killed Mycobacterium tuberculosis). At some time (e.g., at least two weeks) after the first injection, mice are boosted by injection with a second dose of the antigen mixed with incomplete Freund's adjuvant. A few weeks after the second injection, mice are tail bled and the sera titered by immunoprecipitation against radiolabeled antigen. Preferably, the process of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture. Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media. Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

Yet another aspect of the present invention provides for pharmaceutical compositions comprising the variant VP2 protein, pVP2-VP3 empty capsid, synthetic virus or live nonpathogenic virus in combination with a physiologically acceptable carrier. The pharmaceutical compositions of the present invention are typically administered in the water supply, spraying or injection.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

It is clear that a vaccine according to the invention may also contain immunogens related to other pathogens of poultry or may contain nucleic acid sequences encoding these immunogens, like antigens of Infectious Bronchitis Virus, Newcastle Disease virus Infectious Bursal Disease virus or Marek's Disease Virus to produce a multivalent vaccine.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

Alternatively, the present invention provides a process of detecting peptides of the present invention, wherein the process comprises immunoreacting the peptides with antibodies prepared according to a process described above to form an antibody-peptide conjugate and detecting the conjugates.

In yet another aspect, the present invention contemplates a process of screening substances for their ability to interact with the variant VP-2 protein, the process comprising the steps of providing a protein(s) of the present invention and testing the ability of selected substances to interact with the protein(s).

Recombinant peptide expression systems of the present invention possess definite advantages over tissue-based systems. The methods of the present invention make it possible to produce large quantities of variant VP2 peptides for use in screening assays. Screening assays of the present invention generally involve determining the ability of a candidate substance to bind to the peptide. The peptides of the present invention can be coupled to a solid support. The solid support can be agarose beads, polyacrylamide beads, polyacrylic beads or other solid matrices capable of being coupled to proteins. Well known coupling agents include cyanogen bromide, carbonyidiimidazole, tosyl chloride, and glutaraldebyde.

In a typical screening assay for identifying candidate substances, such as antibodies for the variant VP2 peptides, one employs an amount of the peptide(s) and an appropriate assay buffer at an appropriate pH. The candidate substances are added to the admixture in convenient concentrations and the interaction between the candidate substance and the peptide(s) is monitored.

Accordingly, it is proposed that this aspect of the present invention provides those of skill in the art with methodology that allows for the identification of candidate substances, such as variant VP2 peptides to determine an infection by IBDV. In preferred assays, an admixture containing the peptide, effector and candidate substance is allowed to incubate for a selected amount of time, and the resultant incubated mixture subjected to a separation means to separate the unbound effector remaining in the admixture from any effector/peptide complex so produced. Then, one simply measures the amount of each (e.g., versus a control to which no candidate substance has been added). This measurement can be made at various time points where velocity data is desired.

Numerous techniques are known for separating the effector from effector/peptide complex, and all such methods are intended to fall within the scope of the invention. Use of thin layer chromatographic methods (TLC), HPLC, spectrophotometric, gas chromatographic/mass spectrophotometric or NMR analyses. It is contemplated that any such technique can be employed so long as it is capable of differentiating between the effector and complex, and can be used to determine enzymatic function such as by identifying or quantifying the substrate and product.

The present invention provides a process of screening a biological sample for the presence of a variant VP2 protein. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

In accordance with a screening assay process, a biological sample is exposed to an antibody immunoreactive with the VP2 protein whose presence is being assayed. Typically, exposure is accomplished by forming an admixture in a liquid medium that contains both the antibody and the candidate peptide. Either the antibody or the sample with the peptide can be affixed to a solid support (e.g., a column or a microliter plate). The biological sample is exposed to the antibody under biological reaction conditions and for a period of time sufficient for antibody-polypeptide conjugate formation. Biological reaction conditions include ionic composition and concentration, temperature, pH and the like. Ionic composition and concentration can range from that of distilled water to a 2 molar solution of NaCl. Temperature preferably is from about 4° C. to about 100° C. pH is preferably from about a value of 4.0 to a value of about 9.0, more preferably from about a value of 6.5 to a value of about 8.5 and, even more preferably from about a value of 7.0 to a value of about 7.5. The only limit on biological reaction conditions is that the conditions selected allow for antibody-polypeptide conjugate formation and that the conditions do not adversely affect either the antibody or the peptide.

Exposure time will vary with the biological conditions used, the concentration of antibody and peptide and the nature of the sample (e.g., fluid or tissue sample). Means for determining exposure time are well known to one of ordinary skill in the art. Typically, where the sample is fluid and the concentration of peptide in that sample is about $10^{-10}$ M, exposure time is from about 10 minutes to about 200 minutes.

The presence of a variant VP2 peptide in the sample is detected by detecting the formation and presence of antibody-peptide conjugates. Means for detecting such antibody-antigen (e.g., peptide) conjugates or complexes are well known in the art and include such procedures as centrifugation, affinity chromatography and the like, binding of a secondary antibody to the antibody-candidate peptide complex.

In one embodiment, detection is accomplished by detecting an indicator affixed to the antibody. Exemplary and well known such indicators include radioactive labels (e.g., $^{35}$S $^{32}$P, $^{125}$I, $^{14}$C), a second antibody or an enzyme such as horse radish peroxidase. Means for affixing indicators to antibodies are well known in the art. Commercial kits are available.

A DNA molecule and, particularly a probe molecule, can be used for hybridizing as oligonucleotide probes to a DNA source suspected of possessing the variant VP2 peptide encoding polynucleotide or gene. The probing is usually accomplished by hybridizing the oligonucleotide to a DNA source suspected of possessing such a peptide gene. In some cases, the probes constitute only a single probe, and in others, the probes constitute a collection of probes based on a certain amino acid sequence or sequences of the VP2 peptide and account in their diversity for the redundancy inherent in the genetic code.

A suitable source of DNA for probing in this manner can be a genomic library of a cell line of interest. Alternatively, a source of DNA can include total DNA from the cell line of interest. Once the hybridization process of the invention has identified a candidate DNA segment, one confirms that a positive clone as been obtained by further hybridization, restriction enzyme mapping, sequencing and/or expression and testing.

In another aspect, the present invention contemplates a diagnostic assay kit for detecting the presence of antibodies specific for the variant VP2 peptide of the present invention in biological samples, where the kit comprise a first container containing the variant VP2 peptide capable of immunoreacting with antibodies in biological samples, in an amount sufficient to perform at least one assay. Preferably, assay kits of the invention further comprise a second container containing a second antibody that immunoreacts with the first antibody. Preferably the antibodies used in the assay kits of the present invention are monoclonal antibodies. Even more preferably, the peptides are affixed to a solid support. More preferably still, the first and second antibodies comprise an indicator, and, preferably, the indicator is a radioactive label or an enzyme. The reagents of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media or a microscope slide.

In yet another aspect, cDNA clones of IBDV segment A including the variant VP2 protein and segment B are prepared using standard cloning procedures and methods as described in U.S. Pat. Nos. 5,788,970 and 6,231,868, the contents of which are hereby incorporated by reference herein. Synthetic transcripts derived from cloned DNA corresponding to the entire genome of a segmented dsRNA animal virus have been demonstrated to give rise to a replicating virus. The recovery of infectious virus after transfecting cells with synthetic plus-sense RNAs derived from cloned cDNA of a virus with a dsRNA genome (IBDV) completes the quest of generating reverse infectious systems for RNA viruses. Transfection of cells with plus-sense RNAs of segments A and B is sufficient to generate infectious virus (IBDV).

Transfection of plus-sense RNAs from segments A and B into the same cell is necessary for the successful recovery of IBDV. Transfected RNAs of both segments are translated by the cellular translation machinery. The translated protein VP1 of segment B probably acts as a RNA-dependent RNA polymerase and transcribes minus-strands from synthetic plus-strands of both segments, and the reaction products formed dsRNA.

The foregoing aspects and embodiments of the present invention are further described in the following Examples. However, the present invention is not limited by the Examples, and variations will be apparent to those skilled in the art without departing from the scope of the present invention.

EXAMPLE 1

Genomic dsRNAs from Gerogia variant infected bursal homogenates were isolated by digestion with proteinase K (200 μg/ml) for 4 h at 37° C. in a buffer containing 100 mM Tris-HCl pH 7.5, 12 mM EDTA, 150 mM NaCl, and 1% SDS. The samples were extracted twice with phenol/chloroform/isopropanol/mixture (25:24:1). The aqueous phase was ethanol-precipitated, dried, resuspended in a small volume (usually 50 μl) of diethyl pyrocarbonate-treated water (DEPC-$H_2O$), and used for reverse transcription (RT)-PCR analysis.

A set of primers, including BamBV (forward 24-mer primer): 5'-GGGATCCCAGCGATGACAAACCTG-3' (SEQ ID NO: 3), IBDVP2R (reverse 18-mer primer): 5'-CCAATTGCATGGGCTAGG-3' (SEQ ID NO: 4), were used for RT-PCR amplification according to the supplier's protocol (Perkin-Elmer). The resulting fragments were separated by agarose gel electrophoresis, purified by QIAquick gel extraction kit (QIAGEN Inc., Santa Clarita, Calif.), and their DNAs were directly sequenced by dideoxy chain termination method (Sanger et al., 1977). All other manipulations of DNAs were performed according to standard protocols (Sambrook et al., 1989). Construction of a full-length cDNA clone of a IBDV genome has been described previously (Brandt et al., 2001) and the techniques described therein are used for construction of the genome of the Georgia variant strain.

Methods for cloning of genomic segments A and B, have been previously described. (Vakharia et al., 1993). At least three independent cDNA clones of the above-mentioned constructs were sequenced by the dideoxy chain termination method (Sanger et al., 1977), using an automated DNA sequencer (Applied Biosystems), and the sequence data were analyzed using PC/Gene (Intelligenetics) software. The integrity of the full-length constructs was tested by an in vitro transcription-translation-coupled reticulocyte lysate system using T7 RNA polymerase (Promega Corp.). The resulting labeled products were separated on a sodium dodecyl sulfate-12.5% polyacrylamide gel (SDS-PAGE) and visualized by autoradiography (data not shown). Full-length cDNA clones of segments A selected for the recovery of infectious virus.

Radiolabeling of the IBDV proteins was carried out as described (Muller et al., 1982). Embryonated eggs were infected with IBDV at a multiplicity of infection of 10 PFU/cell and incubated at 37° C. After a pulse with $^{35}$S-methionine for 12 hours, labeled virus particles were sedimented from the culture medium and purified further by centrifugation.

Competitive binding assays were performed as described by Robertson et al (Robertson et al., 1984) except that purified $^{35}$S-labeled virus particle antigen is used as the assay antigen.

A number of neutralizing Mabs against various strains of IBDV were used to test their reactivity with different IBDV antigenic variants. Table 1 below shows the reactivity pattern of some Mabs with different antigenic variants of IBDV in an AC-ELISA system. (Snyder et al., 1988).

Reactivity pattern of IBD viruses with a panel of strain-specific Mabs by antigen capture ELISA (AC-ELISA)

| Viruses | Reactivity with Mabs | | | | | |
|---------|-----|-----|----|----|----|---|
|         | B69 | R63 | 57 | 67 | 10 | 8 |
| D78     | +   | +   | −  | −  | +  | + |
| GLS     | −   | −   | +  | −  | +  | + |
| E.Del   | −   | +   | −  | +  | −  | + |
| AL2     | −   | −   | +  | +  | −  | + |
| GA var. | −   | −   | +  | +  | +  | + |
| control | −   | −   | −  | −  | −  | − |

* D78 vaccine strain (classic), GLS variant virus from infected cell cultures, E.Del variant, GA variant (isolated in Georgia), and AL2 viruses from infected bursal homogenates were tested for the reactivity with a panel of strain-specific Mabs. Control, no virus was detected in the bursal homogenates of the uninfected chickens.
+, viral antigen detected by AC-ELISA
−, no viral antigen could by detected by AC-ELISA The variant virus of Georgia comprising the variant VP2 protein has the characteristic of both "GLS" and "Delaware" strains. as it reacts with both Mabs 57 and 67. As shown in Table 1, the Georgia variant reacts with Mabs 57 and 67 indicating that it can identify both GLS and Delaware strains. Interestingly it also reacts with Mabs 10 and 8, which indicates that it can identify the D78 strain.

Changes in the Amino Acid Residues at residues 318 and 359 for VP2 Protein of the GA strain relative to U.S. GLS-5 and E/DEL variants are shown in FIG. 3.

REFERENCES

All references cited herein are hereby incorporated by reference herein for all purposes.

Azad, A. A., Jagadish, M. M., Brown, M. A. et al., 1987, Deletion mapping and expression in *escherichia-coli* of the large genomic segment of a birnavirus, *Virology* 161 (1): 145-152.

M. Brandt, M., Yao, K., Liu, M., Heckert, R. A. and Vakharia, V. N., 2001, Molecular determinants of virulence, cell tropism, and pathogenic phenotype of infectious bursal disease virus, *J. Virol.* 75, pp. 11974-11982.

Chalfie, M., Tu, Y., Euskirchen, G., Ward, W. W., Prasher, D. C. 1994. Green fluorescent protein as a marker for gene expression. *Science* 263: 802-805.

Crameri, A., Whitehorn, E. A., Tate, E., Stemmer, W. P. C., 1996, Improved green fluorescent protein by molecular evolution using DNA shuffling. *Nature Biotechnol.* 14: 315-319.

Dobos, P., Hill, B. J., Hallett, R., Kells, D. T., Becht, H., and Teninges, D., 1979 Biophysical and biochemical characterization of five animal viruses with bisegmented double-stranded RNA genomes, *J. Virol.* 32, pp. 593-605.

Frank, M. B., 1998 Insect Cell Culture & Baculovirus Infections. *In: Molecular Biology Protocols.* (http://omr-f.ouhsc.edu/~frank/baculpro.html).

Hudson, P. J., N. M. McKern, B. E. Power and A. A. Azad, 1986 Genomic structure of the large RNA segment of infectious bursal disease virus, *Nucleic Acids Res.* 14, pp. 5001-5012.

Kibenge, F. S. B., Dhillon, A. S., Russell, R. G., 1988, Biochemistry and immunology of infectious bursal disease virus, *Journal of General Virology* 69: 1757-1775.

Maeda, S., Kawai, T., Obinata, M., Fujiwara, H., Horiuchi, T., Saeki, Y., Sato, Y., Furusawa, M. 1985. Production of human .alpha.-interferon in silkworm using a baculovirus vector. *Nature* 315: 592-594.

Marumoto, Y., Sato, Y., Fujiwara, H., Sakano, K., Sakei, Y., Agata, M., Furusawa, M., Maeda, S. 1987. Hyperproduction of polyhedrin-IGF II fusion protein in silkworm larvae infected with recombinant Bombyx mori nuclear polyhedrus virus. *J. Gen. Virol.* 68: 2599-2606.

Medin, J. A., Hung, L., Gathy, K., Evans, R. K., Coleman, M. S. 1990. Efficient, low-cost protein factories: expression of human adenosine deaminase in baculovirus-infected insect larvae. *Proc. Nat. Acad. Sci. USA* 87: 2760-2764.

Miyajima, A., Schreurs, J., Otsu, K., Kondo, A., Arai, K., Maeda, S., 1987, Use of silkworm, Bombyx mori, and an insect baculovirus vector for high-level expression and secretio of biologically active mouse interleukin-3, *Gene* 58: 273-281.

Muller, H. and Becht, H., J., 1982, Biosynthesis of virus-specific proteins in cells infected with infectious bursal disease virus and their significance as structural elements for infectious virus and incomplete particles, *Journal of Virology* 44 (1): 384-392.

Mundt, E., and V. N. Vakharia, V. N., 1996, Synthetic transcripts of double-stranded birnavirus genome are infectious. *Proc. Natl. Acad. Sci. USA* 93:11131-11136.

O'Reilly, R, Miller, L. K., and V. A Lucklow, V. A, 1992, Baculovirus Expression Vectors: A Laboratory Manual by D (W.H. Freeman and Co., New York, N.Y.).

Prasher, D. C., Eckenrode, V. K., Ward, W. W., Prendergast, F. G., Cormier, M. J, 1992, Primary structure of the Aequorea victoria green fluorescent protein, *Gene*, 111: 229-233.

Robertson, B. H., Morgan, D. O., Moore, D. M. 1984, Location of neutralizing epitopes defined by monoclonal-antibodies generated against the outer capsid polypeptide, vp1, of foot-and-mouth-disease virus-a12, *Virus Research* 1 (6): 489-500.

Sanger, F., Nicklen, S. and A. R. Coulson, 1977, DNA sequencing with chain-terminating inhibitors, *Proc. Natl. Acad. Sci. U.S.A.* 74: pp. 5463-5467.

Sambrook, J., E. F. Fritsch, and T. Maniatis. 1989. Molecular Cloning a laboratory manual. 2nd ed. Cold Spring Harbor Laboratory. Cold Spring Harbor. N.Y.

Shimomura, O., Johnson, F. H., Saiga, Y. 1962. Excitation, purification and properties of aequorin, a bioluminescent protein from the luminous hydromedusan. Aequorea. *J. Cell. Comp. Physiol.* 59: 223-227.

Snyder, D. B., et al., 1988, Proc. 23rd Nat. Meeting Poultry Health Condemn., Ocean City, Md.

Snyder, D. B., Vakharia, V. N., Savage, P. K., 1992, Naturally occurring-neutralizing monoclonal-antibody escape variants define the epidemiology of infectious bursal disease viruses in the United-States, *Achives of Virology* 127 (1-4): 89-101.

Snyder, D. B., Vakharia, V. N., Mengel-whereat, S. A., et al., 1994, Active cross-protection induced by a recombinant baculovirus expressing chimeric infectious bursal disease virus structural proteins, *Avian Diseases* 38 (4): 701-707.

Snyder, D. B., Lana, D. P., Cho, B. R., et al., 1988 Group and strain-specific neutralization sites of infectious bursal disease virus defined with monoclonal-antibodies, *Avian Diseases* 32 (3): 527-534.

Snyder, D. B., Lana, D. P., Savage, P. K., et al, 1988, Differentiation of infectious bursal disease viruses directly from infected-tissues with neutralizing monoclonal-antibodies—evidence of a major antigenic shift in recent field isolates, *Avian Diseases* 32 (3): 535-539.

U.S. Pat. No. 5,595,912, Specific DNA and RNA sequences associated with US IBDV variants, vector carrying DNA sequences, host carrying cloned vector, deduced amino acid sequences, vaccine and method of vaccination, issued on Jan. 21, 1997 to Vakharia, et al.

U.S. Pat. No. 6,231,868, Method for generating nonpathogenic infections birnavirus from synthetic RNA transcripts, issued on May 15, 2001 to Vakharia, et al.

U.S. Pat. No. 5,871,744, Method for generating birnavirus from synthetic RNA transcripts, issued on Feb. 16, 1999 to Vakharia, et al.

U.S. Pat. No. 5,064,646, Novel infectious bursal disease virus, issued on Nov. 12, 1991 to Snyder, et al.

U.S. Patent Application No. 2003/0072772, Sub-unit vaccine for infectious pancreatic necrosis virus, filed on Apr. 17, 2003.

U.S. Pat. No. 5,472,858, Production of Recombinant Proteins in Insect *Larvae*, issued on Dec. 5, 1995 to Attie, et al.

Vakharia, V. N. 1997, Biotechnology Annual Review Volume 3, 151-168,

Vakharia, V. N., Snyder, D. B., He, J., Edwards, G. H., Savage, P. K., and Mengel-Whereat, S. A., 1993, Infectious bursal disease virus structural proteins expressed in a baculovirus recombinant confer protection in chickens, *J. Gen. Virol.* 74, pp. 1201-1206.

WO 95/26196

That which is claimed is:

1. An isolated infectious bursal disease virus (IBDV) Georgia variant strain VP2 protein comprising the amino acid sequence of SEQ ID NO: 5.

2. The isolated infectious bursal disease virus (IBDV) Georgia variant strain VP2 protein of claim 1, encoded by a nucleotide sequence having greater than 97% homology to SEQ ID NO: 6.

3. A live, nonpathogenic IBDV Georgia variant strain comprising at least an expressed VP2 structural protein having the amino acid sequence of SEQ ID NO: 5, wherein a VP5 structural protein is not expressed.

4. A method of generating a live, nonpathogenic Georgia variant IBDV strain, the method comprising the following steps: (a) preparing at least one cDNA of infectious bursal disease virus genome segments A and B, wherein the segment A comprises a VP2 gene of SEQ ID NO: 6 and is modified to prevent expression of NS protein; (b) transcribing said cDNA to produce synthetic RNA transcripts, (c) transfecting host cells with said synthetic RNA transcripts, (d) incubating said host cells in a culture medium, and (e) isolating live, nonpathogenic, infectious bursal disease virus from said culture medium.

5. A method to treat and/or prevent IBDV comprising: administering an effective amount of a sub-unit vaccine comprising the isolated IBDV Georgia variant strain VP2 protein according to claim 1 to breeder chickens to mediate maternal immunity for transference to hatchlings.

6. The method according to claim 5, wherein the sub-unit vaccine is administered through placement in drinking water of the poultry or injection in ovo to embryonated eggs.

7. A method to treat and/or prevent IBDV comprising: administering an effective amount of the live nonpathogenic Georgia variant strain according to claim 3 through placement in drinking water of the poultry, injection in ovo to embryonated eggs or to chickens to mediate maternal immunity for transference to hatchlings.

8. The isolated IBDV VP2 protein of claim 1, wherein the protein is isolated from IBDV Georgia variant strain.

9. The isolated infectious bursal disease virus (IBDV) VP2 protein of claim 2, wherein the nucleoride sequence has 100% homology to SEQ ID NO: 6.

10. A pharmaceutical composition comprising the isolated IBDV VP2 protein of claim 1 and a physiologically acceptable carrier.

11. The pharmaceutical composition of claim 10, further comprising a VP3 structural protein.

12. The phamiaceutical composition of claim 11, wherein the VP3 protein is from a strain different from the Georgia valiant IBDV strain.

13. The pharmaceutical composition of claim 11, wherein the VP2 and VP3 form an empty IBDV viral capsid.

* * * * *

SEQUENCE LISTING

<160> NUMBER OF SEQ ID NOS: 6

<210> SEQ ID NO 1
<211> LENGTH: 1421
<212> TYPE: DNA
<213> ORGANISM: Infectious bursal disease virus

<400> SEQUENCE: 1

```
atgacaaacc tgcaagatca aacccaacag attgttccgt tcatacggag ccttctgatg      60
ccaacaaccg gaccggcgtc cattccggac gacaccctgg agaagcacac tctcaggtca     120
gagacctcga cctacaattt gactgtgggg gacacagggt cagggctaat tgtcttttc     180
cctggattcc ctggctcaat tgtgggtgct cactacacac tgcagagcaa tgggaactac     240
aagttcgatc agatgctcct gactgcccag aacctacctg ccagctacaa ctactgcagg     300
ctagtgagtc ggagtctcac agtaaggtca agcacactcc tggtggcgt ttatgcacta     360
aacggcacca taaacgccgt gaccttccaa ggaagcctga gtgaactgac agatgttagc     420
tacaatggat tgatgtctgc gacagccaac attaacgaca aaattgggaa cgtcctagta     480
ggggaagggg taaccgtcct cagcttaccc acatcatatg atcttgggta tgtgaggctt     540
ggcgacccca tacctgctat agggcttgac ccaaaaatgg tagcaacatg tgacagcagt     600
gacaggccca gagtctacac cataaccgca gccgataatt accaattctc atcacagtac     660
caaacaggcg gggtaacaat cacactgttc tcagccaaca ttgatgccat acaagtctc     720
agtgttgggg gagagctcgt gttcaaaaca agcgtccaaa gccttgtact gggcgccacc     780
atctacctta taggctttga tgggactgcg gtgatcacca gagctgtggc cgcaaacaat     840
gggctgacgg ccggcatcga caatcttatg ccattcaatc ttgtgattcc aaccaatgaa     900
ataacccagc caatcacatc catcaaactg agatagtga cctccaaaag taatggtcag     960
gagggggacc agatgtcatg gtcggcgagt gggagcctag cagtgacgat ccatggtggc    1020
aactatccag gagccctccg tcccgtcaca ctagtggcct acgaaagggt ggcaaaagga    1080
tctgtcgtta cggtcgctgg ggtgagcaac ttcgagctga tcccaaatcc tgaactggca    1140
aagaacctgg ttacagaata cggccgattt gacccaggag ccatgaacta cacaaaattg    1200
atactgagtg agagggaccg tcttggcatc aagaccgtct ggccgacaag ggagtacact    1260
gactttcgcg agtacttcat ggaggtggcc gacctcaact ctcccctgaa gattgcagga    1320
gcatttggct tcaaagacat aatccgggcc ataaggagga tagctgtgcc ggtggtctct    1380
acattgttcc cacctgccgc tcccctagcc catgcaattg g                         1421
```

<210> SEQ ID NO 2
<211> LENGTH: 473
<212> TYPE: PRT
<213> ORGANISM: Infectious bursal disease virus

<400> SEQUENCE: 2

```
Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
                20                  25                  30

Leu Glu Lys His Thr Leu Arg Ser Glu Thr Ser Thr Tyr Asn Leu Thr
            35                  40                  45

Val Gly Asp Thr Gly Ser Gly Leu Ile Val Phe Phe Pro Gly Phe Pro
        50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
                100                 105                 110
```

Leu Pro Gly Gly Val Tyr Ala Leu Asn Gly Thr Ile Asn Ala Val Thr
            115                 120                 125

Phe Gln Gly Ser Leu Ser Glu Leu Thr Asp Val Ser Tyr Asn Gly Leu
        130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asn Tyr Gln Phe Ser Ser Gln Tyr Gln Thr Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val Gln Ser Leu Val
                245                 250                 255

Leu Gly Ala Thr Ile Tyr Leu Ile Gly Phe Asp Gly Thr Ala Val Ile
            260                 265                 270

Thr Arg Ala Val Ala Ala Asn Asn Gly Glu Thr Ala Gly Ile Asp Asn
        275                 280                 285

Leu Met Pro Phe Asn Leu Val Ile Pro Thr Asn Glu Ile Thr Gln Pro
    290                 295                 300

Ile Thr Ser Ile Lys Leu Glu Ile Val Thr Ser Lys Ser Asn Gly Gln
305                 310                 315                 320

Glu Gly Asp Gln Met Ser Trp Ser Ala Ser Gly Ser Leu Ala Val Thr
                325                 330                 335

Ile His Gly Gly Asn Tyr Pro Gly Ala Leu Arg Pro Val Thr Leu Val
            340                 345                 350

Ala Tyr Glu Arg Val Ala Lys Gly Ser Val Val Thr Val Ala Gly Val
        355                 360                 365

Ser Asn Phe Glu Leu Ile Pro Asn Pro Glu Leu Ala Lys Asn Leu Val
    370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala Phe Gly Phe Lys Asp Ile Ile
        435                 440                 445

Arg Ala Ile Arg Arg Ile Ala Val Pro Val Ser Thr Leu Phe Pro
    450                 455                 460

Pro Ala Ala Pro Leu Ala His Ala Ile
465                 470

<210> SEQ ID NO 3
<211> LENGTH: 24
<212> TYPE: DNA
<213> ORGANISM: Artificial
<220> FEATURE:
<223> OTHER INFORMATION: Synthetic construct

<400> SEQUENCE: 3

-continued

```
gggatcccag cgatgacaaa cctg                                            24

<210> SEQ ID NO 4
<211> LENGTH: 18
<212> TYPE: DNA
<213> ORGANISM: Artificial
<220> FEATURE:
<223> OTHER INFORMATION: Synthetic construct

<400> SEQUENCE: 4
ccaattgcat gggctagg                                                   18

<210> SEQ ID NO 5
<211> LENGTH: 441
<212> TYPE: PRT
<213> ORGANISM: Infectious bursal disease virus

<400> SEQUENCE: 5

Met Thr Asn Leu Gln Asp Gln Thr Gln Gln Ile Val Pro Phe Ile Arg
1               5                   10                  15

Ser Leu Leu Met Pro Thr Thr Gly Pro Ala Ser Ile Pro Asp Asp Thr
            20                  25                  30

Leu Glu Lys His Thr Leu Arg Ser Glu Thr Ser Thr Tyr Asn Leu Thr
        35                  40                  45

Val Gly Asp Thr Gly Ser Gly Leu Ile Val Phe Phe Pro Gly Phe Pro
    50                  55                  60

Gly Ser Ile Val Gly Ala His Tyr Thr Leu Gln Ser Asn Gly Asn Tyr
65                  70                  75                  80

Lys Phe Asp Gln Met Leu Leu Thr Ala Gln Asn Leu Pro Ala Ser Tyr
                85                  90                  95

Asn Tyr Cys Arg Leu Val Ser Arg Ser Leu Thr Val Arg Ser Ser Thr
            100                 105                 110

Leu Pro Gly Gly Val Tyr Ala Leu Asn Gly Thr Ile Asn Ala Val Thr
        115                 120                 125

Phe Gln Gly Ser Leu Ser Glu Leu Thr Asp Val Ser Tyr Asn Gly Leu
    130                 135                 140

Met Ser Ala Thr Ala Asn Ile Asn Asp Lys Ile Gly Asn Val Leu Val
145                 150                 155                 160

Gly Glu Gly Val Thr Val Leu Ser Leu Pro Thr Ser Tyr Asp Leu Gly
                165                 170                 175

Tyr Val Arg Leu Gly Asp Pro Ile Pro Ala Ile Gly Leu Asp Pro Lys
            180                 185                 190

Met Val Ala Thr Cys Asp Ser Ser Asp Arg Pro Arg Val Tyr Thr Ile
        195                 200                 205

Thr Ala Ala Asp Asn Tyr Gln Phe Ser Ser Gln Tyr Gln Thr Gly Gly
    210                 215                 220

Val Thr Ile Thr Leu Phe Ser Ala Asn Ile Asp Ala Ile Thr Ser Leu
225                 230                 235                 240

Ser Val Gly Gly Glu Leu Val Phe Lys Thr Ser Val Gln Ser Leu Val
                245                 250                 255

Leu Gly Ala Thr Ile Tyr Leu Ile Gly Phe Asp Gly Thr Ala Val Ile
            260                 265                 270

Thr Arg Ala Val Ala Ala Asn Asn Gly Glu Thr Ala Gly Ile Asp Asn
        275                 280                 285

Leu Met Pro Phe Asn Leu Val Ile Pro Thr Asn Glu Ile Thr Gln Pro
    290                 295                 300
```

```
Ile Thr Ser Ile Lys Leu Glu Ile Val Thr Ser Lys Ser Asn Gly Gln
305                 310                 315                 320

Glu Gly Asp Gln Met Ser Trp Ser Ala Ser Gly Ser Leu Ala Val Thr
            325                 330                 335

Ile His Gly Gly Asn Tyr Pro Gly Ala Leu Arg Pro Val Thr Leu Val
                340                 345                 350

Ala Tyr Glu Arg Val Ala Lys Gly Ser Val Val Thr Val Ala Gly Val
            355                 360                 365

Ser Asn Phe Glu Leu Ile Pro Asn Pro Glu Leu Ala Lys Asn Leu Val
370                 375                 380

Thr Glu Tyr Gly Arg Phe Asp Pro Gly Ala Met Asn Tyr Thr Lys Leu
385                 390                 395                 400

Ile Leu Ser Glu Arg Asp Arg Leu Gly Ile Lys Thr Val Trp Pro Thr
                405                 410                 415

Arg Glu Tyr Thr Asp Phe Arg Glu Tyr Phe Met Glu Val Ala Asp Leu
            420                 425                 430

Asn Ser Pro Leu Lys Ile Ala Gly Ala
            435                 440

<210> SEQ ID NO 6
<211> LENGTH: 1323
<212> TYPE: DNA
<213> ORGANISM: Infectious bursal disease virus

<400> SEQUENCE: 6
atgacaaacc tgcaagatca aacccaacag attgttccgt tcatacggag ccttctgatg      60
ccaacaaccg accggcgtc cattccggac gacaccctgg agaagcacac tctcaggtca     120
gagacctcga cctacaattt gactgtgggg gacacagggt cagggctaat tgtcttttc     180 cctggattcc ctggctcaat tgtgggtgct cactacacac tgcagagcaa tgggaactac     240
aagttcgatc agatgctcct gactgcccag aacctacctg ccagctacaa ctactgcagg     300
ctagtgagtc ggagtctcac agtaaggtca agcacactcc tggtggcgt ttatgcacta     360 aacggcacca taaacgccgt gaccttccaa ggaagcctga gtgaactgac agatgttagc     420
tacaatggat tgatgtctgc gacagccaac attaacgaca aaattgggaa cgtcctagta     480
ggggaagggg taaccgtcct cagcttaccc acatcatatg atcttgggta tgtgaggctt     540
ggcgacccca tacctgctat agggcttgac ccaaaaatgg tagcaacatg tgacagcagt     600
gacaggccca gagtctacac cataaccgca gccgataatt accaattctc atcacagtac     660
caaacaggcg ggtaacaat cacactgttc tcagccaaca ttgatgccat acaagtctc      720 agtgttgggg gagagctcgt gttcaaaaca agcgtccaaa gccttgtact gggcgccacc     780
atctacctta taggctttga tgggactgcg gtgatcacca gagctgtggc cgcaaacaat     840
gggctgacgg ccggcatcga caatcttatg ccattcaatc ttgtgattcc aaccaatgaa     900
ataacccagc aatcacatc catcaaactg agatagtga cctccaaaag taatggtcag     960
gagggggacc agatgtcatg gtcggcgagt gggagcctag cagtgacgat ccatggtggc    1020
aactatccag agccctccg tccgtcaca ctagtggcct acgaaagggt ggcaaaagga    1080
tctgtcgtta cggtcgctgg ggtgagcaac ttcgagctga tcccaaatcc tgaactggca    1140
aagaacctgg ttacagaata cggccgattt gacccaggag ccatgaacta cacaaaattg    1200
atactgagtg agagggaccg tcttggcatc aagaccgtct ggccgacaag ggagtacact    1260
```

```
gactttcgcg agtacttcat ggaggtggcc gacctcaact ctcccctgaa gattgcagga    1320
gca                                                                  1323
```